(12) United States Patent
Walls et al.

(10) Patent No.: US 10,422,736 B2
(45) Date of Patent: Sep. 24, 2019

(54) METHOD FOR DETERMINING POROSITY ASSOCIATED WITH ORGANIC MATTER IN A WELL OR FORMATION

(71) Applicant: Ingrain, Inc., Houston, TX (US)

(72) Inventors: Joel Walls, Houston, TX (US); Anyela Morcote, Houston, TX (US); Yaoming Mu, Houston, TX (US); Marcus Ganz, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 494 days.

(21) Appl. No.: 15/256,758

(22) Filed: Sep. 6, 2016

(65) Prior Publication Data

US 2017/0074772 A1     Mar. 16, 2017

Related U.S. Application Data

(60) Provisional application No. 62/219,363, filed on Sep. 16, 2015.

(51) Int. Cl.
   *G01N 15/08*         (2006.01)
   *G01N 33/24*         (2006.01)
   *G01N 23/225*       (2018.01)

(52) U.S. Cl.
   CPC ......... *G01N 15/088* (2013.01); *G01N 23/225* (2013.01); *G01N 33/24* (2013.01); *G01N 2015/0846* (2013.01)

(58) Field of Classification Search
   CPC .... G01N 15/088; G01N 23/225; G01N 33/24; G01N 2015/0846
   See application file for complete search history.

(56) References Cited

U.S. PATENT DOCUMENTS

| | | | |
|---|---|---|---|
| 4,783,751 A | 11/1988 | Ehrlich et al. | |
| 6,516,080 B1 | 2/2003 | Nur | |
| 7,869,565 B2 | 1/2011 | Wood et al. | |
| 8,155,377 B2 | 4/2012 | Dvorkin et al. | |
| 9,064,328 B2 | 6/2015 | Carpio et al. | |
| 2009/0103677 A1 | 4/2009 | Wood et al. | |
| 2010/0161302 A1 | 6/2010 | Walters et al. | |
| 2013/0182819 A1 | 7/2013 | Dvorkin et al. | |
| 2013/0259190 A1* | 10/2013 | Walls ............... | G01N 23/22 378/9 |
| 2013/0262069 A1 | 10/2013 | Leonard | |
| 2013/0301794 A1* | 11/2013 | Grader ............. | G01N 23/087 378/5 |

(Continued)

FOREIGN PATENT DOCUMENTS

WO     2014011348     1/2014

OTHER PUBLICATIONS

M. Josh, L. Esteban; "Laboratory characterisation of shale properties", Journal of Petroleum Science and Engeneering 88-89, 107-124 (Year: 2012).*

(Continued)

*Primary Examiner* — Regis J Betsch
*Assistant Examiner* — Kaleria Knox
(74) *Attorney, Agent, or Firm* — Chamberlain Hrdlicka (57) ABSTRACT

A method for determining porosity associated with organic matter (PAOM) in a well or formation is provided. A system for performing the method is also provided.

16 Claims, 4 Drawing Sheets

(56) References Cited

U.S. PATENT DOCUMENTS

2014/0052420 A1* 2/2014 Cavanaugh .......... G01N 33/241
703/2

OTHER PUBLICATIONS

Loucks et al., "Morphology, Genesis, and Distribution of Nanometer-Scale Pores in Siliceous Mudstones of the Mississippian Barnett Shale", Journal of Sedimentary Research, 2009, v. 79, pp. 848-861.
Loucks et al., "Preliminary Classification of Matrix Pores in Mudrocks", Gulf Coast Association of Geological Societies Transactions, v. 60, pp. 435-441.
Passey et al., "From Oil-Prone Source Rock to Gas-Producing Shale Reservoir—Geologic and Petrophysical Characterization of Unconventional Shale-Gas Reservoirs", CPS/SPE International Oil & Gas Conference and Exhibition, Beijing, China, SPE 131350, Jun. 8-10, 2010, 29 pages.
International Search Report and Written Opinion issued in corresponding International Patent Application No. PCT/2016/50340 dated Nov. 22, 2016.
Josh et al., "Laboratory characterisation of shale properties," Journal of Petroleum Science and Engineering 88-89, 2012, pp. 107-124.
Maclean O Amabeoku et al: "Evaluation and Application of Digital Rock Physics (DRP) for Special Core Analysis in Carbonate Formations", International Petroleum Technology Conference, Mar. 28, 2013, pp. 26-28, XP055580402.
Walls J et al: "Eagle Ford shale reservoir properties from digital rock physics", First Break European Association of Geoscientists and Engineers, Houten, NL, vol. 29 Jun. 1, 2011, pp. 96-101, XP002696168.
Extended European Search Report, dated May 6, 2019, for European patent application No. 16847067.2, filed on Sep. 6, 2016 (PCT effective date).

* cited by examiner

METHOD FOR DETERMINING POROSITY ASSOCIATED WITH ORGANIC MATTER IN A WELL OR FORMATION

This application claims the benefit under 35 U.S.C. § 119(e) of prior U.S. Provisional Patent Application No. 62/219,363, filed Sep. 16, 2015, which is incorporated in its entirety by reference herein.

FIELD OF THE INVENTION

The present invention relates to a method for determining porosity associated with organic matter in a well or formations. The present invention also relates to systems for the methods.

BACKGROUND OF THE INVENTION

Characterisation of source rocks is important for evaluation of both conventional and unconventional reservoirs. Organic matter is deposited and preserved at the bottom of lakes, seas and deltas. As more material is deposited, the organic matter is buried and the heat and pressure of burial transforms the organic matter into geopolymers such as kerogen and bitumen. When the rocks containing organic matter are buried deep enough, the rocks undergo catagenesis, where temperature begins to convert the kerogen into bitumen and ultimately into hydrocarbons such as oil and gas. The rocks that produce hydrocarbons are referred to as source rocks. Porosity in organic matter is often the predominant type of total porosity development in source rocks. Due to the hydrophobic nature of organic matter, organic porosity, which also can be referred to as porosity associated with organic matter ("PAOM"), is in most situations fully occupied by hydrocarbons, whereas water resides in intra-particle and intergranular pores of inorganic material.

Unconventional resources have emerged as a major source of hydrocarbon production in the United States and other areas. As more information has emerged about these organic rich, fine grained rock formations, often referred to as shale, it has become apparent that the one of the important characteristics is the quantity of porosity that has evolved from what was originally kerogen, bitumen, or other solid organic matter. Porosity in organic matter is a function of the degree of thermal maturity and the resultant decomposition of organic material during the hydrocarbon generation process. From evaluation of high magnification ion-milled SEM images, researchers have observed that shale pore space can be broadly divided into three types, inter-granular, intra-granular and organic matter associated. E.g., Loucks, R. G., et al., 2009, *Morphology, Genesis, and Distribution of Nanometer-Scale Pores in Siliceous Mudstones of the Mississippian Barnett Shale*, Journal of Sedimentary Research, v. 79, p. 848-861, doi: 10.2110/jsr.2009.092; Loucks, R. G., et al., 2010, *Preliminary Classification of Matrix Pores in Mudrocks*, Gulf Coast Association of Geological Societies, Transactions, v. 60, p. 435-441; Passey, Q. R., et al., 2010, *From Oil-Prone Source Rock to Gas-Producing Shale Reservoir-Geologic and Petrophysical Characterization of Unconventional Shale-Gas Reservoirs*, SPE, Chinese Petroleum Society and Society of Petroleum Engineers International Oil and Gas Conference and Exhibition in China, June 8-10, Beijing, China, SPE Paper 131350, 29 p., doi: 10.2118/131350-MS.

Porosity development in organic matter has been observed and organic porosity area calculations have been performed based on such ion milled SEM image analyses. The reliance on ion milled SEM image-based analyses for evaluating geological samples one at a time for PAOM can be problematic since this approach can be time-consuming and costly.

There has not been a reliable method for computing PAOM from commonly available well log data or from core computer tomographic (CT) scan data.

Well log analysis is a common and important part of evaluating hydrocarbon bearing formations for porosity, oil, gas, and water content. Numerous methods exist for computing total and effective porosity from electrical resistivity, bulk density, neutron porosity, and other log analysis measurements. However, shale wells have presented a particularly difficult problem for well log analysis because many traditional methods that work for sandstones and carbonates do not work well for organic shales. There has been no commonly available method to compute PAOM from typical well log data. If certain advanced technology well logs are obtained such as nuclear magnetic resonance or dielectric properties, then it may be theoretically possible to compute PAOM, but these logs are often either unavailable or unreliable in shale formations and are more expensive than common logs like the "triple-combo".

Recently, methods have been developed to compute porosity, clay content, organic matter content and other reservoir properties from bulk density (RHOB) and photoelectric effect (PEF) from X-ray CT scans plus spectral gamma ray data on core samples, which involves integrating a number of different forms of analysis. E.g., U.S. Patent Application Publication No. 2013/0182819 A1. There is no known method, however, to compute PAOM for any location along the length of a whole core from available data such as bulk density, PEF, and spectral gamma ray data.

An equation for directly calculating PAOM from other determined parameter values has been suggested. A suggested equation for calculating PAOM has been expressed as: organic porosity (% rock volume)=TR(fraction)*HI (mg/gTOC)*TOC (% weight)*2.5/1.2/1150, where TR is transformation ratio (the fraction of the labile kerogen that has already converted to petroleum), and HI is hydrogen index when it was immature, and TOC is original TOC, and the constant 2.5 is rock density and 1.2 is kerogen density in g/cc, and 1150 is the equivalent HI of hydrocarbons. The above equation is based on geochemical data and several assumptions. The major unknown in the equation is TR. In order to get a value for TR one has to know the amount of convertible kerogen that has already converted to hydrocarbon. Making this determination of convertible kerogen is not easy and usually requires knowledge of the TOC of the immature kerogen at the location. Data on the immature kerogen is not typically available, and TR has not been simple to quantify. In U.S. Patent Application Publication No. 2014/0052420 A1, a maturity level of a rock sample can be estimated with calculation of a conversion ratio (CR) as PAOM/(PAOM+OM), and the CR may be correlated directly to a maturity level value of the rock sample.

It is desirable to have a method that can be used to more readily determine PAOM for geological samples acquired from a prospective well or formation along the vertical extent, or horizontal extent, or both of a wellbore or formation in a reliable manner. It further is desirable to have such a method for determining PAOM which can use more readily obtainable or commonly available well log data or core CT scan data.

SUMMARY OF THE INVENTION

A feature of the present invention is to provide an improved method for the estimating porosity associated with organic matter of a geological material.

Another feature of the present invention is the incorporation of the indicated method into a process for evaluating the production potential of a well or formation.

A further feature of the present invention is a system for making such determinations.

Another feature of the present invention is to provide a computer readable medium with a computer program product embodied thereon that can be run on one or more computer processors to perform computations and generate results of the indicated methods.

To achieve these and other advantages and in accordance with the purposes of the present invention, as embodied and broadly described herein, the present invention relates, in part, to a method for estimating porosity associated with organic matter in a well or formation, comprising (a) obtaining scanning electron microscope (SEM) or focused ion beam (FIB)-SEM images for a plurality of rock samples obtained from a well or formation, e.g., samples from a whole core, sidewall cores, drill cuttings or other source; (b) determining porosity associated with organic matter (PAOM), total porosity (PHIT), and organic matter (OM) content (TOC), from the SEM or FIB-SEM images; (c) determining maximum apparent transformation ratio (ATR) for the plurality of rock samples using equation (1): ATR=PAOM/(PAOM+OM), wherein the PAOM and OM are determined in (b); (d) curve-fitting a ratio of the PAOM to the PHIT and the TOC for at least three data points obtained in (b) to generate at least one of a mathematical function equation or cross-plot (2) thereof; (e) determining total porosity (PHIT) and organic matter (OM) content (TOC) for a sample of a location along a length of a logged wellbore or core sample of the well or formation; (f) computing a first PAOM for the sample of the logged wellbore or core sample using the mathematical function equation or cross-plot (2) generated using the total porosity (PHIT) and the organic matter (OM) content (TOC) determined in (e); (g) computing a second PAOM for the sample of the logged wellbore or core sample using equation (3): PAOM=ATR×OM/(1−ATR), wherein the ATR is determined in (c) and the OM is determined in (e); (h) comparing the first PAOM calculated from (f) with the second PAOM calculated in (g); and (i) selecting the first PAOM calculated unless the first PAOM is greater than the second PAOM wherein the second PAOM is selected.

The present invention further relates to a method for evaluating the production potential of a well or formation, comprising indicated steps (a)-(i) and further step (j) comprising evaluating the production potential of the well or formation based at least in part on the selected first or second PAOM in (i).

The present invention further relates to a system for estimating porosity associated with organic matter in a well or formation, comprising (a) an SEM or FIB-SEM operable to scan a plurality of rock samples obtained to obtain digital images thereof; (b) one or more computer systems operable for (i) determining porosity associated with organic matter (PAOM), total porosity (PHIT), and organic matter (OM) content (TOC), from the digital images, (ii) determining maximum apparent transformation ratio (ATR) for the plurality of rock samples using equation (1): ATR=PAOM/ (PAOM+OM), wherein the PAOM and OM are determined in (i), (iii) curve-fitting a ratio of the PAOM to the PHIT and the TOC for at least three data points obtained in (i) to generate at least one of a mathematical function equation or cross-plot (2) thereof, (iv) determining total porosity (PHIT) and organic matter (OM) content (TOC) for a sample of a location along a length of a logged wellbore or core sample of the well or formation, (v) computing a first PAOM for the sample of the logged wellbore or core sample using the mathematical function equation or cross-plot (2) generated using the total porosity (PHIT) and the organic matter (OM) content (TOC) determined in (iv), (vi) computing a second PAOM for the sample of the logged wellbore or core sample using equation (3): PAOM=ATR×OM/(1−ATR), wherein the ATR is determined in (ii) and the OM is determined in (iv), (vii) comparing the first PAOM calculated from (v) with the second PAOM calculated in (vi), (viii) selecting the first PAOM calculated unless the first PAOM is greater than the second PAOM wherein the second PAOM is selected, and optionally further (ix) evaluating the production potential of the well or formation based at least in part on the selected first or second PAOM in (viii); and (c) at least one device to display, print, or store results of the computations.

The present invention also relates to a non-transitory computer readable medium with a computer program product embodied thereon that, when performed on a processor in a computerized device provides a method for performing the computations of one or more or all of the indicated steps of the indicated methods.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

DETAILED DESCRIPTION OF THE INVENTION

The present invention relates in part to an improved method for determining porosity associated with organic matter (PAOM) in a well or formation. The method of the present invention can permit a sample at any location along the length of a wellbore or core obtained from a formation to be evaluated for PAOM in relatively rapid and reliable manner. Using rock types for a given well or formation, a calibration curve is generated that mathematically correlates PAOM values with organic matter content (OM) (related to organic content "TOC") and total visible porosity (PHIT). For estimating PAOM in low OM formations, PAOM values are mathematically correlated with maximum apparent transformation ratio (ATR) and organic matter content (OM) as an alternative to using the calibration curve. Using the calibration curve or alternative mathematical relationship, well logging data or core CT scan data can be used in a method of the present invention to reliably compute PAOM values for samples from other locations along the same core or other locations in the same or similar wellbore or formation. These computations of PAOM for other samples using the calibration curve or mathematical relationship can be interpolative or extrapolative. Commonly used methods of well logging or core CT scanning, or other types thereof, can be adapted for use in the method of the present invention. Organic matter content (OM) (or "TOC") and total visible porosity (PHIT) values usually can be determined from commonly used well logging or core CT scanning techniques, whereas reliable PAOM values have not been directly accessible using such techniques. Well logging or core CT scanning methods that can be used to determine organic matter content (OM) (or TOC) and total visible porosity (PHIT) of a sample can be used to provide data inputs to the indicated calibration curve and mathematical relationship used for computing PAOM of a sample according to a method of the present invention. The method of the present invention can reduce the need to analyze SEM images in determining PAOM values for samples located along a core sample or wellbore. The method also can be used to determine PAOM values for samples in a prospective well or formation along the vertical extent, or horizontal extent, or both, of a wellbore or formation. The method can be used to evaluate the production potential of a well or formation.

Figure 3:
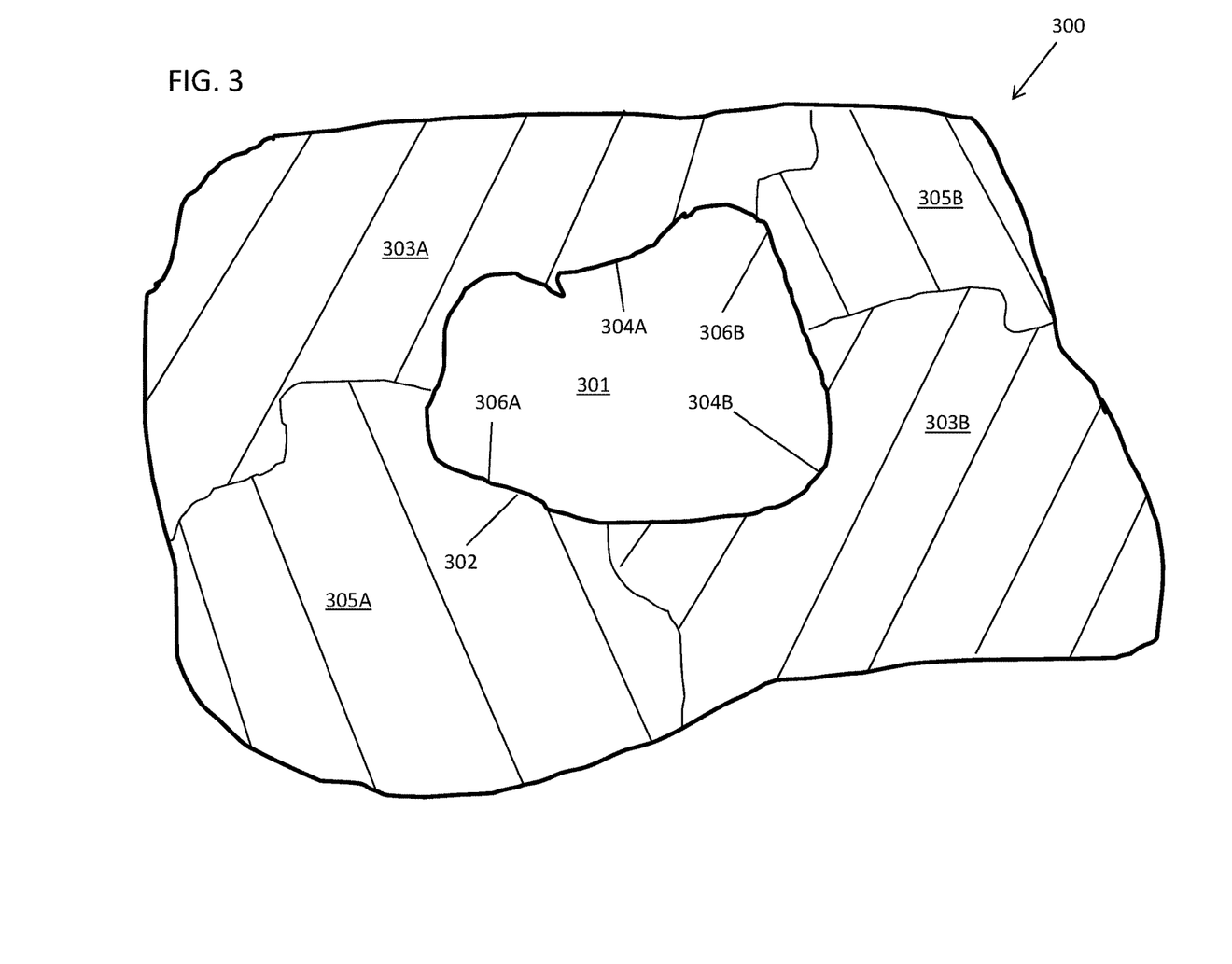
FIG. 3 shows an illustration of a pore space included in an isolated portion of a segmented 2D SEM image of a sample, wherein the a pore perimeter that is partially bounded by organic matter and partially bounded by mineral according to an example of the present application.

The solution provided by the present invention to the indicated prior problems in determining PAOM for source rocks can begin with obtaining 2D SEM images or 3D FIB-SEM image volumes from organic matter-containing rock types obtained from source rock of a given well or formation. The source rock can be a whole core, sidewall plugs, drill cuttings, or other well or formation rock material, which preferably comes from a known depth or depth interval. If the source rock is a whole core, for example, the whole core can be core CT scanned and the scan log can be used to identify and select subsamples, such as plugs, which are extracted from the whole core which contain a range of different organic content. Preferably, subsamples are selected which have relatively higher organic content. Subsamples can be selected which contain from about 1% to about 40%, or from about 2% to about 30%, or from about 4% to about 20% organic content (OM or TOC, vol %), or other ranges. The subsamples, after extraction from the whole core, can be scanned with an SEM to provide a 2D digital image thereof. Alternatively, the subsamples can be first scanned with an SEM to provide a 2D image used to select a site for higher resolution scanning with FIB-SEM, which is used to produce a 3D volume image. Once these images are obtained, processed, and segmented, they can be used to yield quantitative values of porosity, organic matter content (OM), and PAOM. As an option, the SEM or FIB-SEM images can gray scaled and segmented to allocate pixels to different phases including, for example, pores, organic material, mineral, and pyrite (or high density mineral material). PAOM pore regions in the images can be identified by identifying all the pores in the segmented image or images which are directly bounded (bordered) at least in part by organic matter in at least a pre-selected percentage amount. For SEM images, this determination can be made based on a 2D slice view of the sample. The determination of organic matter and non-organic matter pore bounding materials can be done automatically or manually. Since the image can be segmented wherein all the pixels can be classified as pore space, organic matter, mineral, or pyrite, the outer perimeter of a pore space can be identified and the types of directly adjoining material can be identified all the way around the perimeter of the pore space. The total length of a perimeter of a pore space can be determined, and the presence of directly adjoining organic matter and the percentage of the total length of the pore space perimeter that has directly adjoining organic matter can be determined. FIG. 3 shows an illustration of a pore space 301 space included in an isolated portion 300 of a segmented 2D SEM image of a sample that has a pore perimeter 302 (solid line) that is partially bounded by organic matter 303A and 303B at respective length portions 304A and 304B of the pore perimeter 302 and is partially bounded by mineral 305A and 305B at respective length portions 306A and 306B of the pore perimeter 302. Regions 303A and 303B indicate regions of the organic matter that directly bound the pore space 301 and define respective partial length portions of the total pore perimeter 300. The pore space in FIG. 3 is for illustration and the pore spaces can have other geometries. The organic matter may partly or completely bound or surround a pore space.

The pre-selected percentage amount of pore bounding material that must be organic matter for the pore space to be designated PAOM is a value that may vary depending on the formation under evaluation. For shale formations, for example, the pre-selected percentage of the total length of a perimeter of a pore space that must have directly adjoining organic matter for the pore space to be designated PAOM can be selected to be at least 5%, or at least 10%, or at least 20%, or at least 25%, or at least 30%, or at least 40%, or at least 50%, or at least 60%, or at least 70%, or at least 75%, or at least 80%, or at least 90% up to 100%, or other positive values. The total area of PAOM of the sample is determined as a sum of the individual areas of the PAOM-classified pores, i.e., the sum of the individual areas of all the pores in the 2D image that meet the criterion for PAOM classification. PHIT is determined from the image as the total area of all pores, regardless of what kind of material or materials bound the pore. The 3D FIB-SEM image volumes can be constructs of a series 2D SEM images captured of successive exposed surfaces at progressively deeper depths into a sample. For 3D FIB-SEM image volumes, PAOM classification can be determined based on the entire 3D enclosure that partly or completely surrounds each pore. PAOM pore regions in the 3D image volume can be identified by identifying all the pores in the segmented image volume which are directly bounded (bordered) at least in part by organic matter in at least a pre-selected percentage amount. For example, the entire surface area of solid material that surrounds a pore in three dimensions can be analyzed to determine how much of it is organic matter. If the amount meets the pre-selected criterion, then the pore is designated PAOM and its volume is combined with that of the rest of PAOM-classified pores to determine total PAOM. PHIT can be directly determined from the 3D image as the total volume of all pores regardless of what kind of material bounds the pore. Organic matter content, OM, is related to TOC and is sometimes used interchangeably with TOC. OM or TOC can be directly determined from the segmented images.

From this data obtained from the SEM images, "apparent transformation ratio" (ATR) also can be computed using the obtained PAOM and OM values, which is a quantity that tells how much of the original solid organic matter has been converted or transformed into pore space. ATR for SEM and FIB SEM data is defined by Equation (1) as:

$$ATR=PAOM/(PAOM+OM).$$

In the method of the present invention, ATR is measurable on any sample or group of samples that can be obtained from the specific well of interest. It is only necessary to segment the SEM images into organic matter, porosity, and minerals, and then determine how much of the porosity is bounded by organic material as compared to that bounded by solid grains to obtain the PAOM values and corresponding OM values for the samples.

The ratio of PAOM over total visible porosity, PAOM/PHIT, also can be computed wherein PHIT is the sum of PAOM plus intra- and inter-granular porosity. The ratio of organic porosity (PAOM) to total porosity (PHIT) can provide a measure of hydrocarbon saturation.

Figure 1:
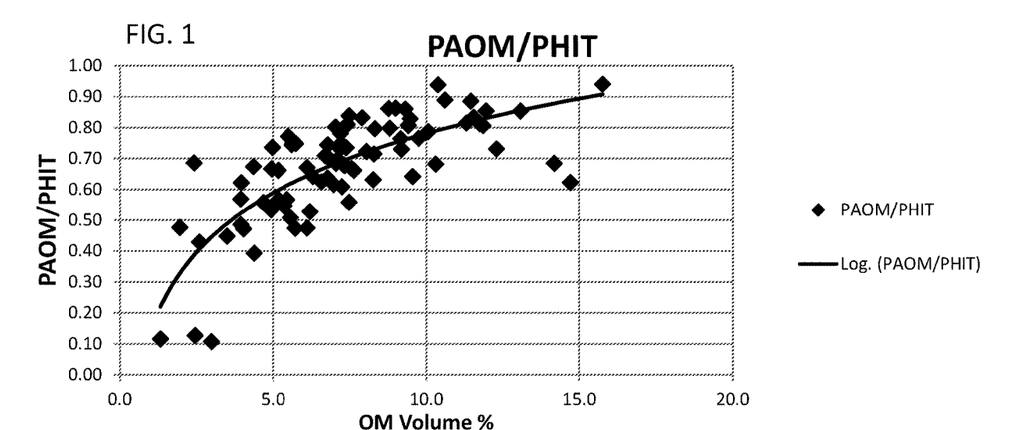
FIG. 1 is a graph showing data for porosity associated with organic matter (PAOM) obtained from 2D SEM images divided by total SEM porosity (PHIT) plotted versus organic matter (OM) content (TOC), and a calibration curve based on curve-fitting the data according to an example of the present application.

A next step of the method of the present invention involves computing some empirical trends, averages, and maximum values for the SEM data and using these to compute how PAOM is related to effective or total image porosity, organic matter, and perhaps clay content. For example, 2D SEM data for one well exhibits a trend, such as shown in FIG. 1. In FIG. 1, PAOM from 2D SEM images divided by total SEM porosity (PHIT) is plotted versus OM content (TOC) (vol. %). The data points are curve fit to generate a calibration curve based thereon. Curve-fitting of data points, such as referenced herein, refers to is the process of constructing a curve, or mathematical function, that has the best fit to a series of data points, possibly subject to constraints. A logarithmic fit is used for curve fitting the data in FIG. 1 which can calculate the least squares fit through points by using the following general equation: y=bln x+a where a and b are constants and ln is the natural logarithm function. This model requires that x>0 for all data points. A nonlinear regression method can be used for this calculation. Statistical mathematical methods for curve fitting data points are generally known and can be implemented with available computer software. Alternatively, PAOM values from 3D FIB-SEM data divided by total SEM porosity can be plotted versus OM content (TOC). These data points also can be curve fit to generate a calibration curve based thereon.

One or both of these trends can be used to compute PAOM from the more easily determined total porosity (PHIT) and TOC that are commonly interpreted from log data or computed from x-ray CT scan plus spectral gamma log data. The general formula for this computation is Equation (2):

$$PAOM=PHIT*a*(Ln(OM)+b)$$

wherein a and b are empirical coefficients. Equation (2) is a first degree polynomial equation. It is noted that this logarithmic equation is just one possible functional form that can be used to fit the data. Other forms can be used as well depending on the nature of the data.

Another possible method is to compute the maximum ATR and then compute PAOM from the following Equation (3):

$$PAOM=ATR*OM/(1-ATR).$$

Figure 2:
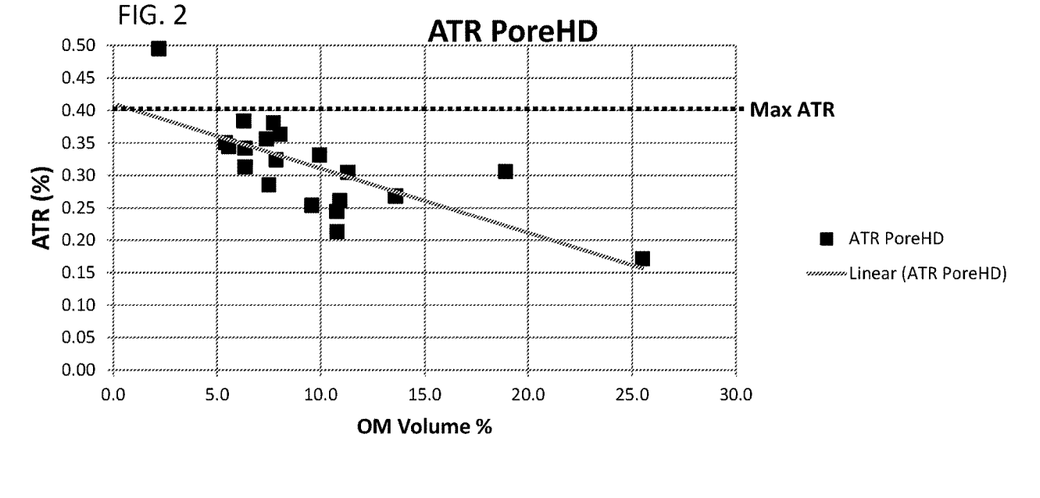
FIG. 2 is a graph showing data for ATR (%) plotted versus OM volume % and a maximum ATR value ("Max ATR") determined from the data according to an example of the present application.

It has been observed that Equation (2) may overestimate PAOM in low OM formations, and that ATR can be quite variable from depth to depth leading to excess scatter from Equation (3). In view of this, a method is provided that combines these two equations so that PAOM is computed from Equation (2) except where it exceeds the value computed from Equation (3), in which case the value from Equation (3) is used. In this case, the maximum ATR is determined from all of the samples from a given well or formation by curve fitting the ATR (%) and OM Volume % data and identifying the maximum ATR on the curve fit line where it extends between 0 OM Volume % and the largest OM Volume % data point plotted (e.g., 26% in FIG. 2), and then use that maximum value for ATR in Equation (3) when determining PAOM for new samples. An illustration of this method is shown in FIG. 2. The curve fit line is a first degree polynomial equation in this illustration. As indicated by the hatched horizontal line in FIG. 2, an ATR value of about 0.40 is the maximum value of ATR on the curve fit line based on the data points plotted in this figure.

Ion-milled SEM or FIB-SEM data may not be required for each individual well if there is sufficient data from other wells in a particular basin or formation. Therefore, the values used in Equations (2) and (3) can be obtained from previous analysis on similar rock types. It is noted that if other trends were observed in the data such as relationships between PAOM and clay content, or between PAOM and gamma ray data, those trends could also be used to improve the resulting predicted PAOM.

There is no known method to compute PAOM along the length of a whole core from available data such as bulk density, PEF, and spectral gamma. This method provides a solution that is based on observations from ion-milled 2D SEM or 3D FIB-SEM data. There is also no commonly available method to compute PAOM from typical well log data. If certain advanced technology well logs are obtained like nuclear magnetic resonance or dielectric properties, then it may be possible to compute PAOM, but these logs are often either unavailable or unreliable in shale formations and are more expensive than common logs like the "triple-combo.

Computing PAOM along the length of a core sample or logged wellbore can help determine oil or gas in place and give an indication of the future production potential of the well or formation. This information can be of high value to oil and gas well operators or owners.

Figure 4:
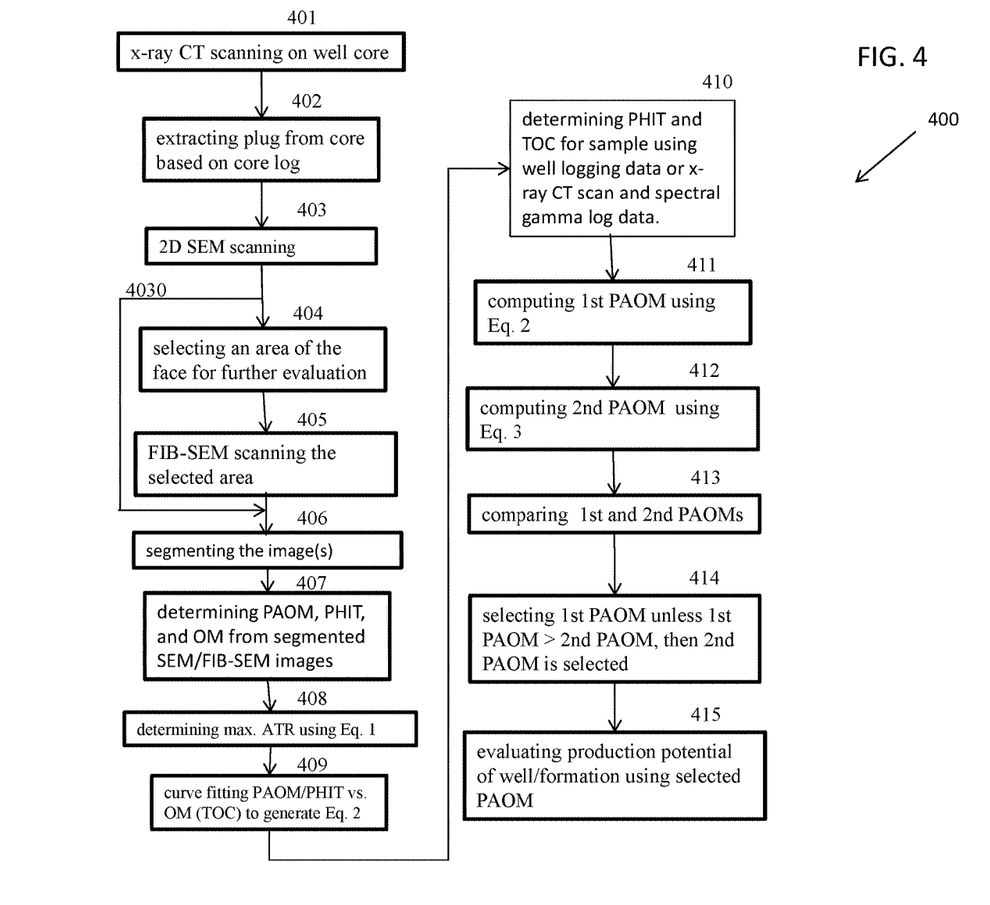
FIG. 4 shows a process flow chart of the determining porosity associated with organic matter for a well or formation according to an example of the present application.

FIG. 4 shows a process flow of a method according to an example of the present invention. The method is shown in the figure as process (400), which can include steps 401-415. The sequence of the steps is indicated by the arrows in the figure, and one or more of the steps can be optional (e.g., step 415) or can represent preferred options. Additional details on these various method steps are proved in the descriptions herein with further reference made to this or other figures. As indicated in FIG. 4, the FIB-SEM imaging related steps 404 and 405 can be bypassed 4030, depending on whether 2D or 3D SEM imaging is selected for use in the method.

The segmentation process that can be used in step 406 can classify individual voxels as either solid or pore. A two- or three-dimensional digital representation can be created of the sample (porous medium), for example, which comprises one or multiple, ordered planes of voxels wherein each of the voxels can represent a pore (pore voxel) or solid (grain voxel). As indicated, preferably more than one type of solid material is identified in the porous medium of the sample, including at least organic matter, and other kinds of solid materials such as mineral and pyrite (or high density material in general). The segmentation process is necessary due to the resolution of the scanner as compared to the size of the grains and pores in the porous medium. A number of methods to segment the 2D or 3D gray scale representation, as applicable, can be used for this purpose. As an example, the sets of image data can be analyzed to allocate or segment pixels in the two-dimensional gray scale images to different phases (e.g., pore space, organic material, mineral or pyrite in some rock samples) to form base analyzed two-dimensional images. The value ascribed to each pixel of the 2D slices is typically an integer that may vary, for example, from zero to 255, for example, where 0 is, e.g., pure black, and 255 is pure white. Such an integer is typically referred to as a "gray scale" value. In the example given, 0 to 255 can be associated, for example, with eight digital bits in a digital word representing the gray scale value in each pixel. Other gray scale ranges may be associated with longer or shorter digital words in other implementations, and the range of 0 to 255 is not intended to limit the scope of the invention. As an option, for the purpose of simulating a process using such a numerical object (the gray scale) for a rock sample, allocating of the pixels can comprise allocating the pixels in the images to pore space, organic matter, mineral or pyrite by determining if the pixel meets preselected threshold criteria based on gray scale values preselected for these classes of material, respectively. The numerical object can be processed, for example, so that all of the pixels allocated to the void space in a rock sample (pore space) are represented by a common numerical value, e.g., by only zeros, and all of the pixels associated with the organic material, rock mineral, or pyrite are represented by different (e.g., progressively higher) numerical values, for example, a value or range value closer to 255 for pyrite (brightest), an intermediate values or range values between that of pyrite and pore for mineral (next brightest) and organic matter. One such method, for example, is described by Nur in U.S. Pat. No. 6,516,080, which is incorporated herein by reference in its entirety. Segmentation processes which can be adapted for use in the present methods are U.S. Pat. Nos. 9,064,328 B2 and 8,155,377 B2, which are incorporated herein by reference in their entirety. Any method capable of producing a digital 2D or 3D representation of a porous medium can be sufficient for the present invention. Gray scaling is a non-limiting example. These and other segmentation methods and techniques may be applied or adapted for use in a method and system of the present invention.

The materials, also referred to herein as the samples, to which the present invention can be applied are not necessarily limited. The materials can be porous geological materials, such as porous rocks, or samples or subsamples thereof. The kinds of rock to which a method of the present invention can be applied are not necessarily limited. The rock sample can be, for example, organic mud rock, shale, carbonate, sandstone, limestone, dolostone, or other rocks, or any combinations thereof, or other kinds. Any source of a rock formation sample of manageable physical size and shape may be used with the present invention. Micro-cores, crushed or broken core pieces, drill cuttings, sidewall cores, outcrop quarrying, whole intact rocks, and the like, may provide suitable rock piece or fragment samples for analysis using methods according to the invention.

Figure 5:
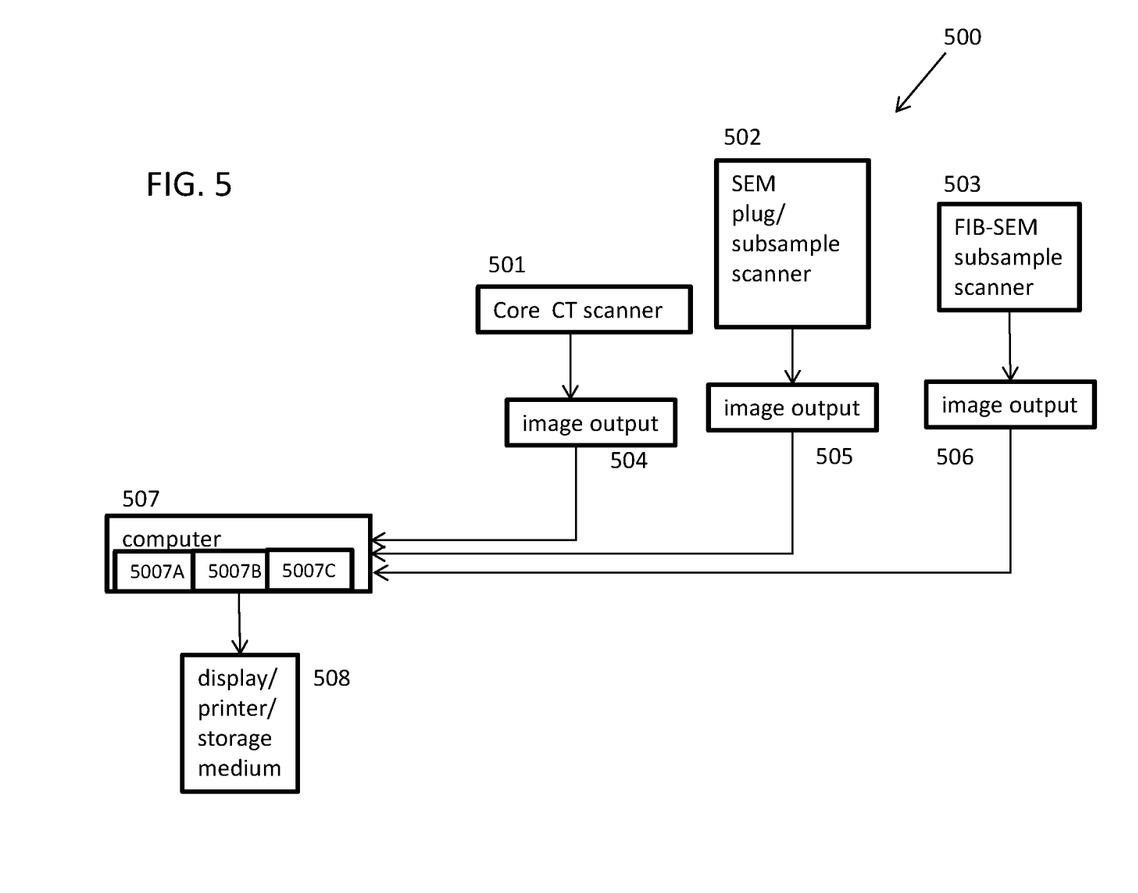
FIG. 5 shows a schematic drawing of a system according to an example of the present application.

Referring to FIG. 5, a system 500 is shown which can be adapted for performing the present methods. As shown in this example, three dimensional (3D) images of the sample obtained from a source are generated by the core CT scanner 501. A two-dimensional SEM image of a sample or samples selected from the sample can be obtained using an SEM scanner 502. A series of 2D images of the sample can be obtained with a FIB-SEM scanner 503 which can be integrated into a 3D image volume by processing of the images at the scanner or an external computer. The image output 504 of the core CT scanner, and at least one of 2D image output 505 of the SEM scanner, and 3D image output 506 of the FIB-SEM scanner can be transferred to a computer 507 having program instructions for carrying out the image analysis, and the indicated data and simulation analysis, to generate sample output/results which can transmitted to one or more devices 508, such as a display, a printer, data storage medium, or combinations of these. The computer programs used for image analysis and the computations can be stored, as a program product, on at least one non-transitory computer usable storage medium 5007B (e.g. a hard disk, a flash memory device, a compact disc, a magnetic tape/disk, or other media) associated with at least one processor 5007A (e.g., a CPU) which is adapted to run the programs, or may be stored on an external computer usable storage medium (not shown) which is accessible to the computer processor. Computer 507 can include at least one non-transitory memory unit or device 5007C for storage of the programs, input data and output data, and other program results, or combinations of these. For output display, device 508 can be, for example, a display monitor, CRT, or other visual means of display (not shown). The computer 507 may include one or more system computers, which may be implemented as a single personal computer or as a network of computers. However, those skilled in the art can appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The units of system 500 including scanners 501, 502, and 503, computer 507, and output display, printer and/or data storage device/medium 508, can be connected to each other for communications (e.g., data transfer, etc.), via any of hardwire, radio frequency communications, telecommunications, internet connection, or other communication means.

The indicated system or apparatus of the present invention may be suitable for analysing material in a laboratory in a building, or in-the-field, such as in a mobile transport vehicle or mechanism on the ground or underground.

The present invention includes the following aspects/embodiments/features in any order and/or in any combination:

1. A method for estimating porosity associated with organic matter in a well or formation, comprising:

(a) obtaining scanning electron microscope (SEM) or focused ion beam (FIB)-SEM images for a plurality of rock samples (e.g., two or more samples, such as 2-5 or more, 2-10 or more, 3-10 or more 5-15 or more) obtained from a well or formation;

(b) determining porosity associated with organic matter (PAOM), total porosity (PHIT), and organic matter (OM) content (TOC), from the SEM or FIB-SEM images (e.g., from all of the images or some of the images or one of the images);

(c) determining maximum apparent transformation ratio (ATR) for the plurality of rock samples using equation (1): ATR=PAOM/(PAOM+OM), wherein the PAOM and OM are determined in (b);

(d) curve-fitting a ratio of the PAOM to the PHIT and the TOC for at least three data points obtained in (b) to generate at least one of a mathematical function equation or cross-plot (2) thereof;

(e) determining total porosity (PHIT) and organic matter (OM) content (TOC) for a sample (e.g., can be any length or size) of a location along a length of a logged wellbore or core sample of the well or formation;

(f) computing a first PAOM for the sample of the core sample or the logged wellbore using the mathematical function equation or cross-plot (2) generated using the total porosity (PHIT) and the organic matter (OM) content (TOC) determined in (e);

(g) computing a second PAOM for the sample of the logged wellbore or core sample using equation (3): PAOM=ATR× OM/(1−ATR), wherein the ATR is determined in (c) and the OM is determined in (e);

(h) comparing the first PAOM calculated from (f) with the second PAOM calculated in (g); and (i) selecting the first PAOM calculated unless the first PAOM is greater than the second PAOM wherein the second PAOM is selected.

2. The method of any preceding or following embodiment/feature/aspect, wherein the well or formation comprises shale.

3. The method of any preceding or following embodiment/feature/aspect, wherein the plurality of rock samples in (a) are whole cores, sidewall cores, drill cuttings, or outcrop quarrying samples.

4. The method of any preceding or following embodiment/feature/aspect, wherein the determining of porosity associated with organic matter (PAOM), total porosity (PHIT), and organic matter (OM) content (TOC) in (b) comprises segmenting the SEM images into organic matter and porosity, and determining quantity of porosity that is bounded by organic material as compared to that bounded by solid grains.

5. The method of any preceding or following embodiment/feature/aspect, wherein the determining of total porosity (PHIT) and organic matter (OM) content (TOC) in (e) comprises interpreting PHIT and TOC from well logging data.

6. The method of any preceding or following embodiment/feature/aspect, wherein the determining of total porosity (PHIT) and organic matter (OM) content (TOC) in (e) comprises computing PHIT and TOC from x-ray CT scan and spectral gamma log data.

7. The present invention also relates to a method for evaluating the production potential of a well or formation, comprising:

(a) obtaining scanning electron microscope (SEM) or focused ion beam (FIB)-SEM images for a plurality of rock samples (e.g., two or more samples, such as 2-5 or more, 2-10 or more, 3-10 or more 5-15 or more) obtained from a well or formation;

(b) determining porosity associated with organic matter (PAOM), total porosity (PHIT), and organic matter (OM) content (TOC), from the SEM or FIB-SEM images (e.g., from all of the images or some of the images or one of the images);

(c) determining maximum apparent transformation ratio (ATR) for the plurality of rock samples using equation (1): ATR=PAOM/(PAOM+OM), wherein the PAOM and OM are determined in (b);

(d) curve-fitting a ratio of the PAOM to the PHIT and the TOC for at least three data points obtained in (b) to generate at least one of a mathematical function equation or cross-plot (2) thereof;

(e) determining total porosity (PHIT) and organic matter (OM) content (TOC) for a sample (e.g., can be any length or size) of a location along a length of a logged wellbore or core sample of the well or formation;

(f) computing a first PAOM for the sample of the logged wellbore or core sample using the mathematical function equation or cross-plot (2) generated using the total porosity (PHIT) and the organic matter (OM) content (TOC) determined in (e);

(g) computing a second PAOM for the sample of the logged wellbore or core sample using equation (3): PAOM=ATR× OM/(1−ATR), wherein the ATR is determined in (c) and the OM is determined in (e);

(h) comparing the first PAOM calculated from (f) with the second PAOM calculated in (g); and (i) selecting the first PAOM calculated unless the first PAOM is greater than the second PAOM wherein the second PAOM is selected; and (j) evaluating the production potential of the well or formation based at least in part on the selected first or second PAOM in (i).

8. The method of any preceding or following embodiment/feature/aspect, further comprising (k) producing at least one of petroleum and natural gas from the well or formation.

9. The method of any preceding or following embodiment/feature/aspect, wherein the well or formation comprises shale.

10. The method of any preceding or following embodiment/feature/aspect, wherein the plurality of rock samples in (a) are whole cores, sidewall cores, drill cuttings, or outcrop quarrying samples.

11. The method of any preceding or following embodiment/feature/aspect, wherein the determining of porosity associated with organic matter (PAOM), total porosity (PHIT), and organic matter (OM) content (TOC) in (b) comprises segmenting the SEM images into organic matter and porosity, and determining quantity of porosity that is bounded by organic material as compared to that bounded by solid grains.

12. The method of any preceding or following embodiment/feature/aspect, wherein the determining of total porosity (PHIT) and organic matter (OM) content (TOC) in (e) comprises interpreting PHIT and TOC from well logging data.

13. The method of any preceding or following embodiment/feature/aspect, wherein the determining of total porosity (PHIT) and organic matter (OM) content (TOC) in (e) comprises computing PHIT and TOC from x-ray CT scan and spectral gamma log data.

14. The present invention further relates to a system for estimating porosity associated with organic matter in a well or formation, comprising:

(a) an SEM or FIB-SEM operable to scan a plurality of rock samples (e.g., two or more samples, such as 2-5 or more, 2-10 or more, 3-10 or more 5-15 or more) obtained to obtain digital images thereof;

(b) one or more computer systems operable for (i) determining porosity associated with organic matter (PAOM), total porosity (PHIT), and organic matter (OM) content (TOC), from the digital images, (ii) determining maximum apparent transformation ratio (ATR) for the plurality of rock samples using equation (1): ATR=PAOM/(PAOM+OM), wherein the PAOM and OM are determined in (i), (iii)

curve-fitting a ratio of the PAOM to the PHIT and the TOC for at least three data points obtained in (i) to generate at least one of a mathematical function equation or cross-plot (2) thereof, (iv) determining total porosity (PHIT) and organic matter (OM) content (TOC) for a sample of a location along a length of a logged wellbore or core sample of the well or formation, (v) computing a first PAOM for the sample of the logged wellbore or core sample using the mathematical function equation or cross-plot (2) generated using the total porosity (PHIT) and the organic matter (OM) content (TOC) determined in (iv), (vi) computing a second PAOM for the sample of the logged wellbore or core sample using equation (3): PAOM=ATR×OM/(1−ATR), wherein the ATR is determined in (ii) and the OM is determined in (iv), (vii) comparing the first PAOM calculated from (v) with the second PAOM calculated in (vi), (viii) selecting the first PAOM calculated unless the first PAOM is greater than the second PAOM wherein the second PAOM is selected, and optionally further (ix) evaluating the production potential of the well or formation based at least in part on the selected first or second PAOM in (viii); and (c) at least one device to display, print, or store results of the computations. 15. The present invention also relates to a non-transitory computer readable medium with a computer program product embodied thereon that, when performed on a processor in a computerized device provides a method for performing computations of one or more or all of the indicated steps of any preceding method.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for estimating porosity associated with organic matter (PAOM) in a well or formation, comprising:
   (a) using a scanning electron microscope (SEM) or a focused ion beam (FIB)-SEM to obtain SEM or FIB-SEM images for a plurality of first rock samples obtained from the well or formation;
   (b) determining PAOM, total porosity (PHIT), and organic matter (OM) content (TOC), from the SEM or FIB-SEM images;
   (c) determining maximum apparent transformation ratio (ATR) for the plurality of rock samples using equation (1): ATR=PAOM/(PAOM+OM), wherein the PAOM and OM are determined in (b);
   (d) curve-fitting a ratio of the PAOM to the PHIT and the TOC for at least three data points obtained in (b) to generate at least one of a mathematical function equation or cross-plot (2) thereof;
   (e) determining total porosity (PHIT) and organic matter (OM) content (TOC) for a second sample of a location along a length of a logged wellbore or core sample of the well or formation;
   (f) computing a first estimated PAOM for the sample of the logged wellbore or core sample using the mathematical function equation or cross-plot (2) generated using the total porosity (PHIT) and the organic matter (OM) content (TOC) determined in (e);
   (g) computing a second estimated PAOM for the sample of the logged wellbore or core sample using equation (3): PAOM=ATR×OM/(1−ATR), wherein the ATR is determined in (c) and the OM is determined in (e);
   (h) comparing the first estimated PAOM calculated from (f) with the second estimated PAOM calculated in (g); and
   (i) selecting the first estimated PAOM unless the first estimated PAOM is greater than the second estimated PAOM wherein the second PAOM is selected.

2. The method of claim 1, wherein the well or formation comprises shale.

3. The method of claim 1, wherein the plurality of rock samples in (a) are whole cores, sidewall cores, drill cuttings, or outcrop quarrying samples.

4. The method of claim 1, wherein the determining of porosity associated with organic matter (PAOM), total porosity (PHIT), and organic matter (OM) content (TOC) in (b) comprises segmenting the SEM images into organic matter and porosity, and determining quantity of porosity that is bounded by organic material as compared to that bounded by solid grains.

5. The method of claim 1, wherein the determining of total porosity (PHIT) and organic matter (OM) content (TOC) in (e) comprises interpreting PHIT and TOC from well logging data.

6. The method of claim 1, wherein the determining of total porosity (PHIT) and organic matter (OM) content (TOC) in (e) comprises computing PHIT and TOC from x-ray CT scan and spectral gamma log data.

7. A method for evaluating the production potential of a well or formation, comprising:
   (a) using a scanning electron microscope (SEM) or focused ion beam (FIB)-SEM to obtain SEM or FIB-SEM images for a plurality of first rock samples obtained from a well or formation;
   (b) determining porosity associated with organic matter (PAOM), total porosity (PHIT), and organic matter (OM) content (TOC), from the SEM or FIB-SEM images;
   (c) determining maximum apparent transformation ratio (ATR) for the plurality of rock samples using equation (1): ATR=PAOM/(PAOM+OM), wherein the PAOM and OM are determined in (b);
   (d) curve-fitting a ratio of the PAOM to the PHIT and the TOC for at least three data points obtained in (b) to generate at least one of a mathematical function equation or cross-plot (2) thereof;
   (e) determining total porosity (PHIT) and organic matter (OM) content (TOC) for a second sample of a location along a length of a logged wellbore or core sample of the well or formation;

(f) computing a first PAOM for the sample of the logged wellbore or core sample using the mathematical function equation or cross-plot (2) generated using the total porosity (PHIT) and the organic matter (OM) content (TOC) determined in (e);

(g) computing a second PAOM for the sample of the logged wellbore or core sample using equation (3): PAOM=ATR×OM/(1−ATR), wherein the ATR is determined in (c) and the OM is determined in (e);

(h) comparing the first PAOM calculated from (f) with the second PAOM calculated in (g); and (i) selecting the first PAOM calculated unless the first PAOM is greater than the second PAOM wherein the second PAOM is selected; and (j) evaluating the production potential of the well or formation based at least in part on the selected first or second PAOM in (i).

8. The method of claim 7, further comprising (k) producing at least one of petroleum and natural gas from the well or formation.

9. The method of claim 7, wherein the well or formation comprises shale.

10. The method of claim 7, wherein the plurality of rock samples in (a) are whole cores, sidewall cores, drill cuttings, or outcrop quarrying samples.

11. The method of claim 7, wherein the determining of porosity associated with organic matter (PAOM), total porosity (PHIT), and organic matter (OM) content (TOC) in (b) comprises segmenting the SEM images into organic matter and porosity, and determining quantity of porosity that is bounded by organic material as compared to that bounded by solid grains.

12. The method of claim 7, wherein the determining of total porosity (PHIT) and organic matter (OM) content (TOC) in (e) comprises interpreting PHIT and TOC from well logging data.

13. The method of claim 7, wherein the determining of total porosity (PHIT) and organic matter (OM) content (TOC) in (e) comprises computing PHIT and TOC from x-ray CT scan and spectral gamma log data.

14. A system for estimating porosity associated with organic matter in a well or formation, comprising:

(a) an SEM or FIB-SEM operable to scan a plurality of rock samples obtained to obtain digital images thereof;

(b) one or more computer systems operable for (i) determining porosity associated with organic matter (PAOM), total porosity (PHIT), and organic matter (OM) content (TOC), from the digital images, (ii) determining maximum apparent transformation ratio (ATR) for the plurality of rock samples using equation (1): ATR=PAOM/(PAOM+OM), wherein the PAOM and OM are determined in (i), (iii) curve-fitting a ratio of the PAOM to the PHIT and the TOC for at least three data points obtained in (i) to generate at least one of a mathematical function equation or cross-plot (2) thereof, (iv) determining total porosity (PHIT) and organic matter (OM) content (TOC) for a sample of a location along a length of a logged wellbore or core sample of the well or formation, (v) computing a first PAOM for the sample of the logged wellbore or core sample using the mathematical function equation or cross-plot (2) generated using the total porosity (PHIT) and the organic matter (OM) content (TOC) determined in (iv), (vi) computing a second PAOM for the sample of the logged wellbore or core sample using equation (3):

PAOM=ATR×OM/(1−ATR), wherein the ATR is determined in (ii) and the OM is determined in (iv), (vii) comparing the first PAOM calculated from (v) with the second PAOM calculated in (vi), (viii) selecting the first PAOM calculated unless the first PAOM is greater than the second PAOM wherein the second PAOM is selected, and optionally further (ix) evaluating the production potential of the well or formation based at least in part on the selected first or second PAOM in (viii); and (c) at least one device to display, print, or store results of the computations.

15. A non-transitory computer readable medium with a computer program product embodied thereon that, when performed on a processor in a computerized device provides a method for performing computations of one or more or all of the indicated steps of the method of claim 1.

16. A non-transitory computer readable medium with a computer program product embodied thereon that, when performed on a processor in a computerized device provides a method for performing computations of one or more or all of the indicated steps of the method of claim 7.

* * * * *